US012629191B2

(12) United States Patent
Solitro et al.

(10) Patent No.: US 12,629,191 B2
(45) Date of Patent: May 19, 2026

(54) PELVIC INTERNAL FIXATION DEVICE AND METHODS OF USING THE SAME

(71) Applicant: Board of Supervisors of Louisiana State University and Agricultural and Mechanical College, Baton Rouge, LA (US)

(72) Inventors: Giovanni Francesco Solitro, Shreveport, LA (US); R. Shane Barton, Shreveport, LA (US); Massimo Morandi, Shreveport, LA (US); Brad Chauvin, Shreveport, LA (US)

( * ) Notice: Subject to any disclaimer, the term of this patent is extended or adjusted under 35 U.S.C. 154(b) by 173 days.

(21) Appl. No.: 18/280,417

(22) PCT Filed: Mar. 4, 2022

(86) PCT No.: PCT/US2022/018962
§ 371 (c)(1),
(2) Date: Sep. 5, 2023

(87) PCT Pub. No.: WO2022/187662
PCT Pub. Date: Sep. 9, 2022

(65) Prior Publication Data
US 2024/0148422 A1 May 9, 2024

Related U.S. Application Data

(60) Provisional application No. 63/156,603, filed on Mar. 4, 2021.

(51) Int. Cl.
A61B 17/86 (2006.01)

(52) U.S. Cl.
CPC ........ *A61B 17/863* (2013.01); *A61B 17/8605* (2013.01); *A61B 17/8685* (2013.01)

(58) Field of Classification Search
CPC ............ A61B 17/6433; A61B 17/7037; A61B 17/7007; A61B 17/863
See application file for complete search history.

(56) References Cited

U.S. PATENT DOCUMENTS

| | | | |
|---|---|---|---|
| 8,398,635 B2 | 3/2013 | Vaidya | |
| 8,900,278 B2 | 12/2014 | Vaidya | |
| 9,517,095 B2 | 12/2016 | Vaidya | |
| 2008/0016853 A1 | 1/2008 | Zhang et al. | |
| 2008/0161853 A1 | 7/2008 | Arnold et al. | |
| 2010/0217334 A1* | 8/2010 | Hawkes ............. | A61B 17/7005 29/446 |
| 2012/0221055 A1 | 8/2012 | Copf | |
| 2012/0259370 A1 | 10/2012 | Vaidya | |
| 2014/0088650 A1 | 3/2014 | Taddia et al. | |
| 2017/0135733 A1 | 5/2017 | Donner et al. | |

OTHER PUBLICATIONS

Al-Ajmi, A. et al. Iatrogenic femoral neuropathy: Two cases and literature update. J Clin Neuromuscul Dis (2010), 12(2), 10 pages.

(Continued)

*Primary Examiner* — Olivia C Chang
(74) *Attorney, Agent, or Firm* — Baker, Donelson, Bearman, Caldwell & Berkowitz, PC

(57) ABSTRACT
Aspects of the invention are drawn to a pelvic internal fixation system and methods of using the same to fix one hemipelvis to the other.

14 Claims, 9 Drawing Sheets

(56)  References Cited

OTHER PUBLICATIONS

Apivatthakakul, T. et al. "Anterior subcutaneous pelvic internal fixator (INFIX), Is it safe?" A cadaveric study. Injury, 47(10), 2077-2080, (2016).

Cavalcanti Kussmaul, A. et al. Biomechanical comparison of minimally invasive treatment options for Type C unstable fractures of the pelvic ring. Rev Chir Orthop Traumatol 106 (2020) 127-133.

Cole, PA, et al. Minimally-invasive fixation for anterior pelvic ring disruptions. Injury 46 S3 (2015) S27-S34.

Fang, C. et al. Complications after percutaneous internal fixator for anterior pelvic ring injuries. Int Orthop 2017;41:1785-90.

Hesse, D. et al. Femoral nerve palsy after pelvic fracture treated with INFIX: A case series. Journal of Orthopaedic Trauma, 29(3), 138-143, (2015).

Hua, X. et al. Minimally invasive internal fixator for unstable pelvic ring injuries with a pedicle screw-rod system: a retrospective study of 23 patients after 13.5 months. Arch Orthop Trauma Surg 2019; 139:489-96.

Melhem, E. et al. Epidemiology of pelvic and acetabular fractures in France. Rev Chir Orthop Traumatol 2020;106:488-96.

Morandi, M. "Max," et al. Safe Supra-Acetabular Pin Insertion in Relation to Intraosseous Depth. Journal of Orthopaedic Research, (2019).

Okuyama, K. et al. Influence of bone mineral density on pedicle screw fixation: a study of pedicle screw fixation augmenting posterior lumbar interbody fusion in elderly patients. Spine J Off J North Am Spine Soc 2001; 1:402-7.

Osterhoff, G. et al. Anterior subcutaneous internal fixation of the pelvis—what rod-to-bone distance is anatomically optimal? Injury (2017) 48:2162-8.

Scherer, J. et al. Subcutaneous internal anterior fixation of pelvis fractures—which configuration of the InFix is clinically optimal?—a retrospective study. Int Orthop 2019;43:2161-6.

Scheyerer. MJ. et al. Anterior subcutaneous internal fixation for treatment of unstable pelvic fractures. BMC Res Notes 2014;7:133, 10 pages.

Vaidya, R. et al. Anterior Subcutaneous Internal Pelvic Fixation / INFIX☐: A Systemic Review. Orthop Trauma (2018) 32:24-30.

Vaidya, R. et al. Combined Pelvic Ring Disruption and Acetabular Fracture: Outcomes Using a Sequential Reduction Protocol and an Anterior Subcutaneous Pelvic Fixator (INFIX). J Orthop Trauma (2019) 33:S66-S71.

Vaidya, R, et al. Complications of anterior subcutaneous internal fixation for unstable pelvis fractures: A multicenter study trauma. Clin Orthop Relat Res 2012; 470:2124-31.

Vaidya, R. et al. The bikini area and bikini line as a location for anterior subcutaneous pelvic fixation: An anatomic and clinical investigation. Clin Anat 2013;26:392-9.

Vaidya, R. et al. Treatment of unstable pelvic ring injuries with an internal anterior fixator and posterior fixation: Initial clinical series. J Orthop Trauma 26(1): p. 1-8, Jan. 2012.

Vigdorchik, JM et al. Biomechanical stability of a supra-acetabular pedicle screw Internal Fixation device (INFIX) vs External Fixation and plates for vertically unstable pelvic fractures. J Orthop Surg Res (2012) 7:31, 6 pages.

Vigdorchik, JM. et al. Anterior internal fixator versus a femoral distractor and external fixation for sacroiliac joint compression and single stance gait testing: A mechanical study in synthetic bone. Int Orthop (2013), 37:1341-1346.

Yin, Y. et al. Complications following internal fixator in the treatment of pelvic fracture. Orthopedics (2018) 42(1), 8 pages.

International Search Report for PCT/US2022/018962 mailed Jun. 10, 2022.

Written Opinion for for PCT/US2022/018962 mailed Jun. 10, 2022.

* cited by examiner a)

b)

c)

a)

b)

c)

a)

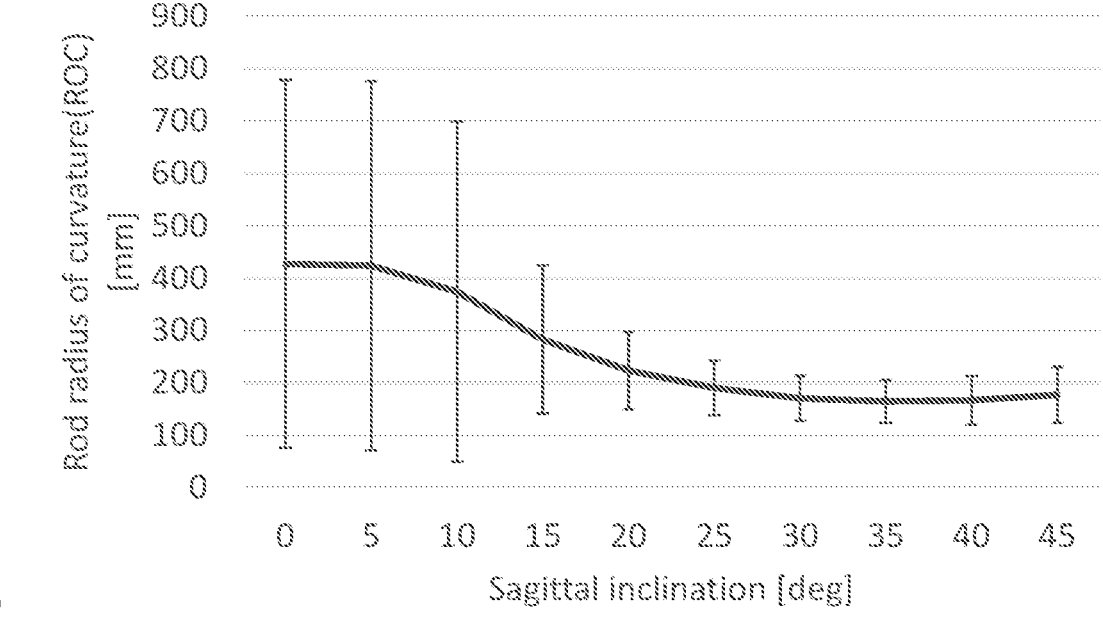
b)
FIG. 17 CON'T

PELVIC INTERNAL FIXATION DEVICE AND METHODS OF USING THE SAME

This application is a national phase application of PCT Application PCT/US2022/018962 filed on Mar. 4, 2022 which claims priority from U.S. Provisional Application No. 62/156,603 filed on Mar. 4, 2021, the entire contents of each of which is incorporated herein by reference in its entirety.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

Aspects of the invention are drawn to a pelvic internal fixation system and methods of using the same to fix one hemipelvis to the other.

BACKGROUND OF THE INVENTION

Pelvic ring fractures account for 1.5% of adult fractures and 2-5% of fractures that require inpatient admission which can be from high energy trauma or standing height falls in osteoporotic patients. The pelvic subcutaneous internal fixation (PSIF) is one potential treatment option for displaced pelvic ring injuries.

SUMMARY OF THE INVENTION

The present invention provides a surgical device, wherein the device comprises at least one bone screw, a bone screw head connector, and a rod, wherein the rod is connected to the bone screw via the bone screw head connector.

In embodiments, the bone screw comprises a screw head and a threaded body.

In embodiments, the screw head comprises a spherical head.

In embodiments, the bone screw head connector comprises a polyaxial bone screw head connector.

In embodiments, the bone screw head connector comprises a bone screw head receiving end, a middle base, and a rod attachment end.

In embodiments, the bone screw head receiving end is configured to pair with the screw head of the bone screw.

In embodiments, the rod attachment end is configured to pair with one end of the rod.

In embodiments, the rod attachment end comprises a polyaxial head.

In embodiments, the rod attachment end comprises a spherical head.

In embodiments, the length of the rod attachment end relative to the middle base is adjustable.

In embodiments, the middle base comprises an inner portion configured to allow the length of the rod attachment end to be adjusted.

In embodiments, the inner portion of the middle base is configured to pair with an insert affixed to the rod attachment end, and wherein the placement of the insert within the inner portion is adjustable, thereby allowing for the length of the rod attachment end to be adjusted relative to the inner base.

In embodiments, the rod comprises at least one receiving end, wherein the receiving end is configured to attach to the rod attachment end of the bone screw head connector.

In embodiments, the at least one end of the rod is configured to attach to the polyaxial head of the bone screw head connector.

In embodiments, the length of the rod is adjustable.

In embodiments, the rod comprises a telescoping rod.

In embodiments, the rod is curved.

In embodiments, the rod terminates at the bone screw head connector.

Aspects of the invention are also drawn towards a surgical device according to any one of FIG. 1-FIG. 12.

Still further, aspects of the invention are drawn towards a method for implanting the surgical device as described herein into a subject. For example, the method comprises: inserting the bone screw into a bone of a subject, coupling the bone screw head connector to the bone screw head, determining the appropriate angle of the head of the bone screw head connector relative to surrounding anatomical structures, and immobilizing the bone screw head connector; coupling the rod to the bone screw head connector, determining the appropriate angle of the rod relative to abdominal organs and musculature, and immobilizing the rod, thereby implanting the surgical device into a subject.

In embodiments, the bone comprises a pelvic bone.

In embodiments, the bone is a fractured bone.

Other objects and advantages of this invention will become readily apparent from the ensuing description.

DETAILED DESCRIPTION OF THE INVENTION

Figure 1:
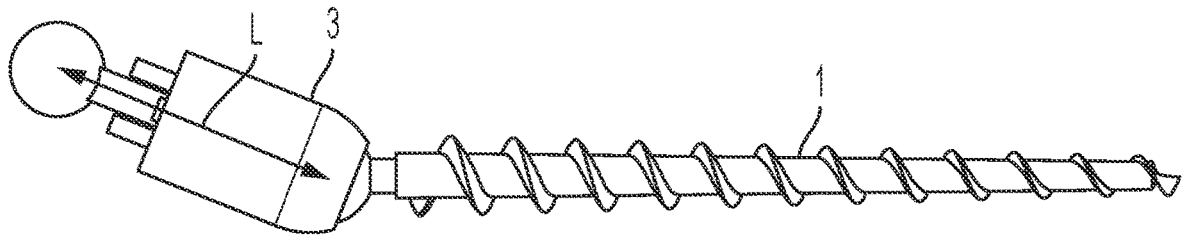
FIG. 1 is one perspective of a bone screw comprising a spherical head and a threaded body under one embodiment. The spherical head of the bone screw is connected to a polyaxial bone screw head connector. The length (L) of the polyaxial bone screw head connector can be adjustable.

Detailed descriptions of one or more embodiments are provided herein. It is to be understood, however, that the present invention can be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification can mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly, "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein, the term "about" can refer to approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

For purposes of the present disclosure, it is noted that spatially relative terms, such as "up," "down," "right," "left," "beneath," "below," "lower," "above," "upper" and the like, can be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device can be otherwise oriented (rotated 90 degrees or at other orientations) and the spatially relative descriptors used herein interpreted accordingly.

As used herein, the term "standard of care" can refer to a diagnostic and/or treatment process for which a clinician follows for a certain type of patient, illness, or clinical circumstance. For example, a standard of care can refer to the ordinary level of skill and care that a clinician is expected to observe in providing clinical care to a patient. In embodiments, the standard of care can vary depending on the patient, the illness, or clinical circumstance. As used herein, "standard care practices" can refer to practices which are standard of care.

As used herein, the term "clinician" can refer to a person qualified in the clinical practice of medicine, psychiatry, or psychology. As used herein, the terms "clinician" and "practitioner" can be used interchangeably. For example, "clinician" can refer to a physician, a surgeon, a veterinarian, a physician assistant, a nurse, or a person practicing under the supervision thereof.

As used herein, the term "board-certified" can refer to a professional whose qualifications have been approved by an official group or governing body. For example, the person is a physician who has graduated from medical school, completed residency, trained under supervision in a specialty, and passed a qualifying exam given by a medical specialty board.

The terms "subject" and "patient" as used herein include all members of the animal kingdom including, but not limited to, mammals, animals (e.g., cats, dogs, horses, swine, etc.) and humans.

The term "surgical device" can refer to the term "surgical device" refers to any device or component that can be used to operate on tissue (e.g., to treat, manipulate, handle, hold, cut, heat, or energize, etc., tissue).

Described herein are non-limiting, exemplary embodiments for clinical use of the surgical device(s) described herein. As standard of care is determined by the type of patient, illness, and clinical situation, the embodiments described herein are non-limiting and exemplary in nature and can be adapted for standard of care practice by one of ordinary skill in the art. For example, one of ordinary skill comprises a board-certified physician, board certified surgeon, or a person practicing under the supervision thereof.

Pelvic Internal Fixation Device

Aspects of the invention are drawn to a pelvic internal fixation device and methods of use thereof.

Referring to FIG. 1, for example, the device can comprise at least one 1 bone screw and a 3 bone screw head connector.

The term 1 bone screw can refer to an implant designed to be implanted or inserted into a bone as part of a surgical device. The 1 bone screw can comprise a screw head and a threaded body.

Figure 3:
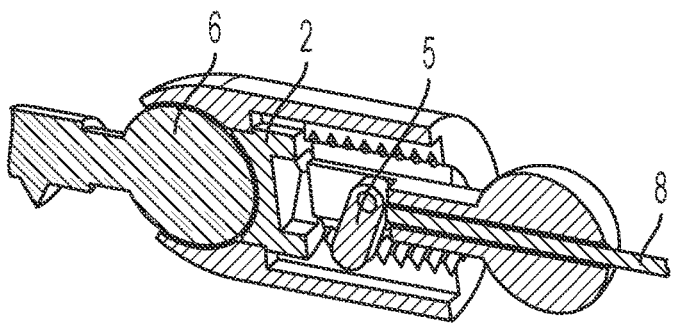
FIG. 3 shows a cutaway thereof. The bone screw receiving end is configured to pair with the head of the bone screw, and the rod attachment end comprises an adjustable, spherical head that is configured to pair with the rod. The bottom panel shows the threaded inner portion of the middle base and an insert affixed to the rod attachment end which allows the length of the rod attachment end to be adjusted.

The term "screw head" can refer to the portion of the screw to which torque is applied. FIG. 3, for example, provides an embodiment wherein the screw head is spherical. The screw head can be any shape so long as it pairs or mates with the receiving end of the screw head connector.

The term "thread" can refer to the helical protruding portion on the body of a screw which engages or displaces surrounding material (e.g., bone) with which the screw comes in contact. In embodiments, the threaded body can be a male threaded body. In embodiments, the threaded body can be a female threaded body.

In embodiments, the threaded body of the 1 bone screw can be tapered. The term "taper" or "tapered" can refer to an elongated structure with a gradual diminution of width or thickness. In embodiments, the diameter of the body can be between about 4.5 mm and about 9.5 mm. For example, the diameter of the body can be about 4.5 mm, about 5.0 mm, about 5.5 mm, about 6.0 mm, about 6.5 mm, about 7.0 mm, about 7.5 mm, about 8.0 mm, about 8.5 mm, about 9.0 mm, or about 9.5 mm.

In embodiments, the screw length of the screw body can be about 50 mm to about 200 mm. For example, the length of the screw body can be about 50 mm, about 60 mm, about 70 mm, about 80 mm, about 90 mm, about 100 mm, about 110 mm, about 120 mm, about 130 mm, about 140 mm, about 150 mm, about 160 mm, about 170 mm, about 180 mm, about 190 mm, or about 200 mm.

It will be understood that changing the angle at which the screw is inserted into the bone allows one to change the length of the screw body which engages or displaces the bone. For example, the wider the angle of insertion, the shorter the insertion length needed. An aspect of the invention allows for the screw body to be inserted into the bone at an optimal angle for maximal strength without consideration of the angle of the screw head connector or the rod. Once the screw is inserted into the bone at an optimal angle, the polyaxial screw head connector can be adjusted to connect to the rod. Therefore, aspects of the invention allow for optimization of the screw length and rod also the rod angle.

The 3 bone screw head connector (or head connector) is configured to attach to the screw head of the 1 bone screw. In embodiments, the bone screw head connector comprises a polyaxial bone screw head connector. The term "polyaxial" can refer to the ability of one element, such as the polyaxial bone screw head connector, to deflect a significant amount, i.e. greater than 10 degrees, in all directions relative to the 1 bone screw.

Figure 2:
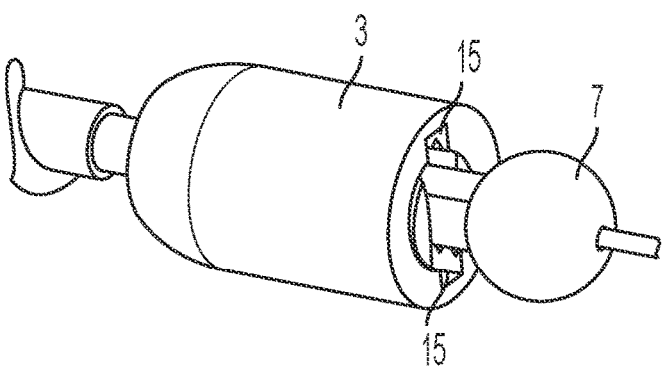
FIG. 2 is one perspective of a polyaxial bone screw head connector under one embodiment.

Referring to FIG. 2, the 3 bone screw head connector comprises a bone screw receiving end, a middle base, and a 7 rod attachment end.

The bone screw receiving end is configured to pair or mate with the screw head of the 1 bone screw. As shown in FIG. 1, for example, the 1 bone screw can comprise a male head that pairs or mates with a female bone screw receiving end. In an alternative embodiment, the 1 bone screw can comprise a female head that pairs or maters with a male bone screw receiving end.

The middle base of the bone screw head connector can comprise a hallowed inner portion with components configured to allow the length (L) of the 7 rod attachment end to be adjusted. FIG. 3, for example, provides one embodiment where the inner portion of the middle base is configured to pair with a 5 insert operably affixed to the 7 rod attachment end. Placement of the 5 insert within the inner portion is adjustable, thereby allowing for the length of the 7 rod attachment end to be adjusted relative to the middle base.

The 7 rod attachment end of the bone screw head connector can comprise an inner portion that is configured to pair with the inner portion of the middle base, and an exterior portion that is configured to pair with the 4 rod. For example, the 7 rod attachment end comprises a head that is configured to pair or mate with a receiving end of the 4 rod. FIG. 2, for example, provides one embodiment wherein the head of the 7 rod attachment end is spherical. The 7 head of the rod attachment end can be any shape so long as it pairs or mates with the receiving end of the 4 rod.

Figure 11:
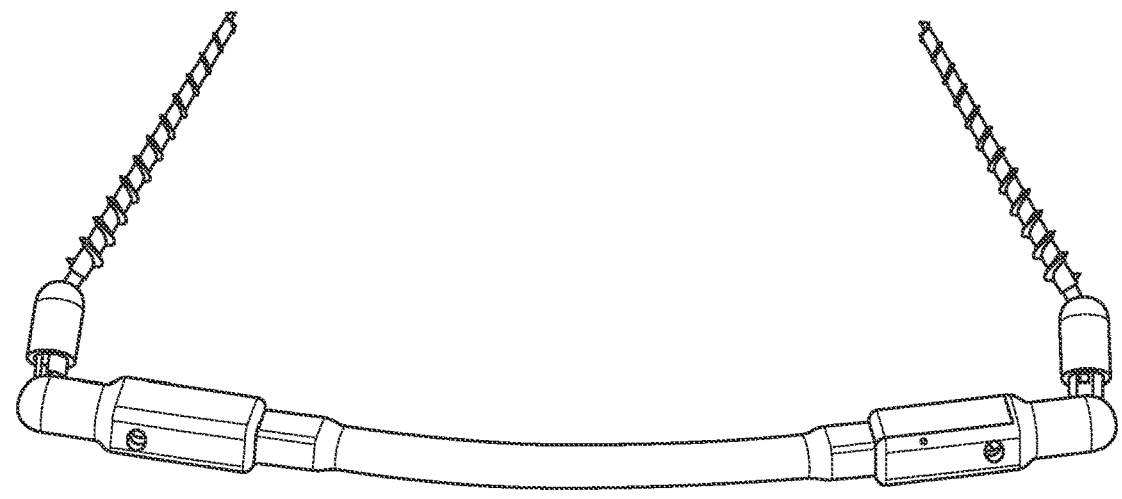
FIG. 11 is a schematic of one embodiment of the invention assembled.

Referring to FIG. 11, the pelvic internal fixation device further comprises a 4 rod. In embodiments, a 1 bone screw and 3 bone screw head connector can be implanted into a subject in each hemipelvis, and a 4 rod can be attached to each bone screw head connector, thus fixing the hemipelvis together. As such, the 4 rod can comprise at least one end or two ends that are configured to attach the 7 rod attachment end of the 3 bone screw head connector.

Figure 7:
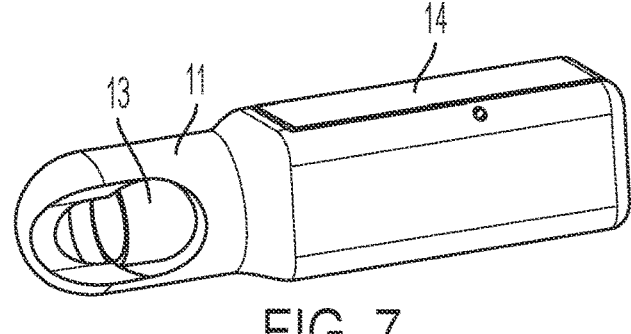
FIG. 7 is one perspective of an end of the rod that is configured to attach to the rod attachment end of the bone screw head connector under one embodiment.
Figure 8:
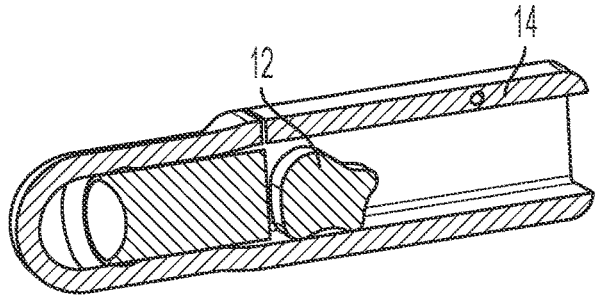
FIG. 8 is a cut-away of the end of the rod that is configured to attach to the rod attachment end of the bone screw head connector under one embodiment. The attachment end of the rod can comprise a sliding mechanism that is configured to allow the length of the rod to be adjusted.
Figure 9:
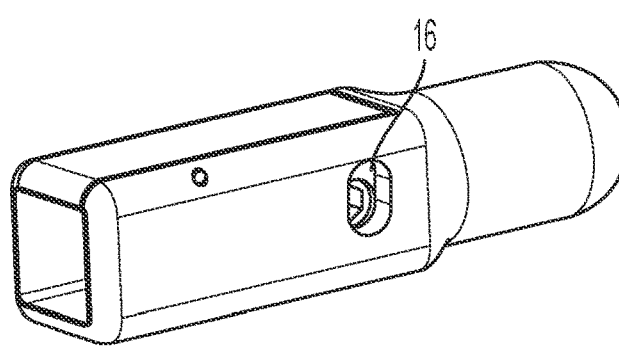
FIG. 9 is one perspective of the end of the rod that is configured to attach to the rod attachment end of the bone screw head connector under one embodiment.
Figure 10:
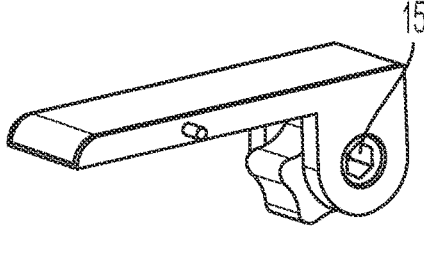
FIG. 10 is a schematic of the eccentric gear hosted in the lever that can be rotated through a polygonal connection accessible through a slot created in the sliding attachment (SA).

As shown in FIG. 11, the one or both ends of the rod are configured to attach to the rod attachment end of the bone screw head connector. FIG. 7 and FIG. 8, for example, provide one embodiment of a receiving end of the 4 rod, wherein the 11 receiving end comprises a 13 portion for maiting or pairing with the bone screw head connector, and a 14 portion for maiting or pairing with the 4 rod. In embodiments, the 14 portion for maiting or pairing with the 4 rod can be male (and the rod can be female), or the 14 portion for maiting or pairing with the 4 rod can be female (and the rod will be male).

Referring to FIG. 8, embodiments can comprise a 12 locking mechanism, which functions to lock the 4 rod into place.

In embodiments, the length of the 4 rod must be sufficient to span the distance from one hemipelvis to the other, such as between about 200 mm and about 700 mm. For example, the length of the rod can be about 200 mm, about 250 mm, about 300 mm, about 350 mm, about 400 mm, about 450 mm, about 500 mm, about 550 mm, about 600 mm, about 650 mm, or about 700 mm.

In embodiments, the length of the 4 rod can be fixed or, in embodiments, the length can be adjustable prior to being implanted into the subject. For example, the length of the 4 rod can be adjustable by about 10 mm, about 20 mm, about 30 mm, about 40 mm, or about 50 mm.

In embodiments, the rod can be a telescoping rod, thereby allowing the length of the rod to be adjusted. As used herein, telescoping can refer to a nested extendable member that includes at least one intermediate member between two engaging members. In embodiments, the rod can be cut to a particular length.

In embodiments, the 4 rod can be curved. In an exemplary embodiment, the curvature and rigidity of the rod mimicks the natural rigidity of the pelvis. For example, the curvature and rigidity of the rod is such that the motion resembles that of the natural pelvis in the body of the subject.

In embodiments, the 4 rod can have a diameter of about 5.5 mm to about 15 mm. For example, the diameter of the rod can be about 5.5 mm, about 6.0 mm, about 7.5 mm, about 8.0 mm, about 8.5 mm, about 9 mm, about 9.5 mm, about 10 mm, about 10.5 mm, about 11 mm, about 11.5 mm, about 12 mm, about 12.5 mm, about 13 mm, about 13.5 mm, about 14 mm, about 14.5 mm or about 15 mm.

In embodiments, the 4 rod terminates at the bone screw head connector. This prevents infection and/or irritation caused by rod ends that otherwise can extend past the hemipelvis.

Figure 4:
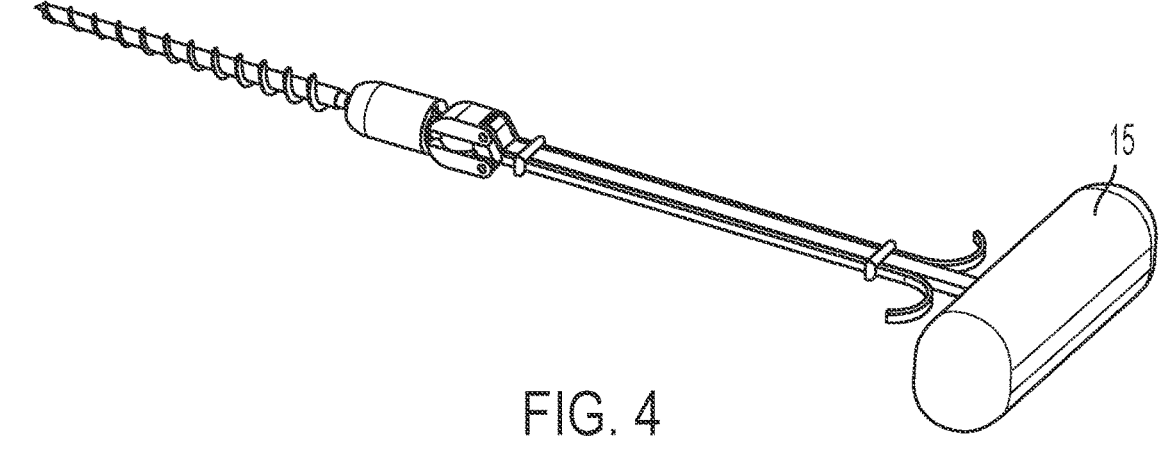
FIG. 4 is a schematic of a tool that controls placement of the threaded insert within the bone screw head connector under one embodiment. The tool has claws configured to attached to the rod attachment end of the bone screw head connector and can further secure the insert within the bone screw head connector to control its rotation. The surgeon can regulate the length (L) of the bone screw head connector by rotating the tool.

Referring to FIG. 4, embodiments comprise a tool that controls placement of the 5 insert within the bone screw head connector, thereby adjusting the length of the rod attachment end. The tool has a 15 handle on one end and 9 claws on the opposite end, whereby the 9 claws are config- ured to attached to the rod attachment end of the bone screw head connector and can further secure the insert within the bone screw head connector to control its rotation. The surgeon can regulate the length (L) of the bone screw head connector by rotating the tool.

Figure 5:
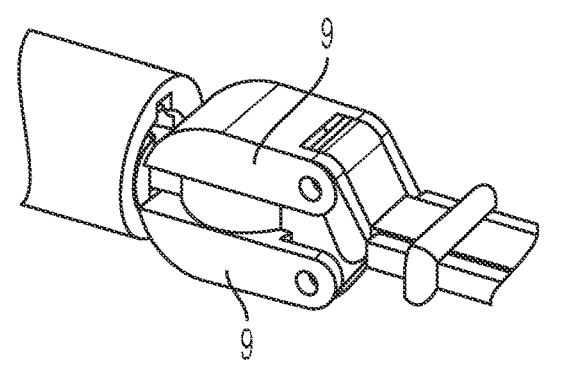
FIG. 5 is one perspective of the claws attached to the rod attachment end of the bone screw head connector.
Figure 6:
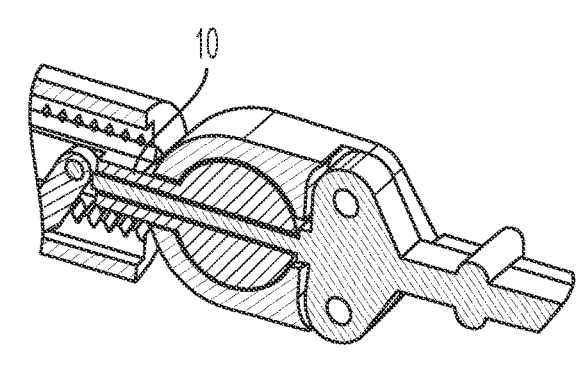
FIG. 6 is a cutaway thereof. As shown in the cut-away, the rod attachment end can comprise a channel through which the insert (and thereby the length (L) of the rod attachment end) can be adjusted by the tool.

FIG. 5 provides one perspective of the 9 claws attached to the rod attachment end of the bone screw head connector. As shown in FIG. 6, the rod attachment end can comprise a 10 channel through which the 5 insert (and thereby the length (L) of the rod attachment end) can be adjusted by the tool.

In embodiments, components of the device described herein, such as the bone screw, bone screw head connector, and rod, can be fabricated from any biocompatible material. The term "biocompatible material" can refer to any material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood. Non-limiting examples include titanium, stainless steel, cobalt chrome, carbon fiber, and the like.

Aspects of the invention are also drawn towards methods for implanting the pelvic internal fixation device as described herein into a subject. The term "implanting" can refer to.$ inserting or embedding a medical device surgically into or onto a subject.

The pelvis is a basin-shaped structure that supports the spinal column and protects abdominal organs. The pelvis contains the sacrum, the coccyx, and three hip bones (in- cluding the illium, pubis, and ischium). Pelvic surgery for trauma can require stabilization of the left and right wings of the pelvis. External fixater can be too far away from the bone to provide optimal stability, and are also prone to infection. Therefore, aspects of the invention herein provide devices and methods for internal pelvic fixation.

Figure 12:
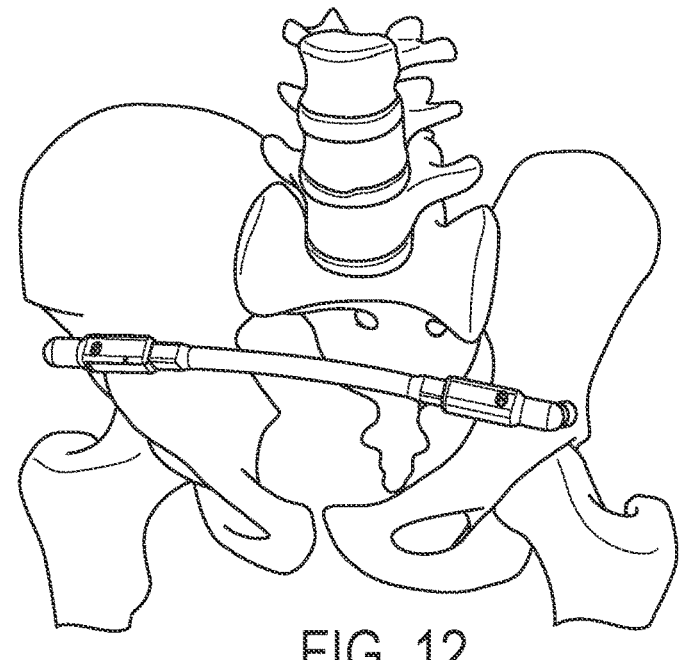
FIG. 12 is a schematic of one embodiment of the invention applied to a model of the human skeleton.

A pelvic fracture can require considerable force. Most pelvic fractures are caused by direct blows or by a blow through the thighbone (femur). Pelvic fractures are often the result of motor vehicle accidents, especially motorcycle accidents. Embodiments as described herein can fix one hemipelvis to the other. FIG. 12, for example, provides one embodiment of the device fixing one hemipelvis to the other.

In an embodiment, the patient can be positioned accord- ing to standard of care, and the device can subsequently be implanted according to the standard of care for implanting such a pelvic fixation device. In embodiments, the method comprises inserting the bone screw into a bone of a patient, coupling the bone screw head connector to the bone screw head, determining the appropriate angle of the head of the bone screw head connector relative to surrounding anatomi- cal structures, and immobilizing the bone screw head con- nector; coupling the rod to the bone screw head connector, determining the appropriate angle of the rod relative to abdominal organs and musculature, and immobilizing the rod, thereby implanting the surgical device into a subject.

EXAMPLES

Examples are provided below to facilitate a more com- plete understanding of the invention. The following examples illustrate the exemplary modes of making and practicing the invention. However, the scope of the inven- tion is not limited to specific embodiments disclosed in these Examples, which are for purposes of illustration only, since alternative methods can be utilized to obtain similar results.

Example 1— Hardware and Tools for Pelvic Subcutaneous Anterior Internal Fixation The invention comprises a device made of various com- ponents assembled to provide pelvic anterior stability fol- lowing fracture. Referring to the figures, for example, the components thereof can comprise:

A bone screw (1) for each hemipelvis that can be char- acterized by a spherical head that can be secured through a set screw (2) to a "polyaxial" head connector (3) in a manner that the main axis of the head connector does not need to be the axis of the screw.

A rod connecting the two hemipelves that is connected to the two screws through a lock mechanism that limits relative rotation and displacement when enabled.

A bone screw head connector that can also be equipped with a spherical head, so the rod axis does not need to be perpendicular to the screw head connector axis. The screw head connector can be of variable length (L).

The variability in length of the screw head connector (SHC) (3) can be obtained through a screw mechanism:
the inner surface of the screw head connector is internally threaded and hosts a threaded insert with spherical head (4) that is limited in its rotation by the enabling of a lever (5) that fits in slots (6) hosted in the screw head connector. The limit set by the lever on the rotation of the threaded insert results in the retention of the length L (see FIG. 2).

The lever is pressed outward from the threaded insert by a spring element and is pushed inward by a pin (7) inserted trough the screw head.

The threaded insert is positioned in place through a tool (8) that attaches to the spherical head and has claws (9) shaped to host the spherical head and secure the flat shoulder of the inner insert (10) to control its rotation, so the surgeon by rotating the tool regulates the length L.

The attachment between the spherical head of the screw head connector and the rod connecting the hemipelves can be done through a polyaxial mechanism such as what can be adopted for spine screws or it can be done through a sliding attachment (SA) here described. The sliding attachment (SA) is conceived to allow the inner sliding of the rod so the surgeon can reduce the fracture without the need of cutting the rod. The SA has an opening (11) to allow insertion of the screw head connector spherical head and through the rotation of an eccentric gear (12), it is secured the angulation of the spherical head and the position of the rod. The eccentric gear, on one side presses a cylinder (13) on the spherical head while on the other side presses a lever (14) that constrain the rod in its position. In an embodiment the rod has polygonal terminal sections to ease the rotational constraint.

The eccentric gear is hosted in the lever and can be rotated through a polygonal connection (15) accessible through a slot (16) created in the SA.

Example 2

The internal anterior fixation as in U.S. Pat. No. 8,900,278B2 is performed with screws and rods used for spine surgeries. The stabilization of the two hemipelves is performed inserting the screws leaving the screw head at a certain gap distance from the bone to avoid femoral nerve palsy that results in residual quadriceps weakness and/or gait disturbance and connecting the two screws with a rod that in most of the cases protrudes outward the screws causing pain in correspondence of the lateral femoral cutaneous nerve.

U.S. Pat. No. 9,517,095B2 and U.S. Pat. No. 8,398,635B2 provide implants designed for this surgery, but are not available on the marked devices labeled for this procedure and surgeries are performed with hardware conceived for the spine.

Furthermore, existing devices used are limited in their safety by the fact that the screw head must be spaced from the bone and such spacing is done along the direction of the screw axis.

U.S. Pat. No. 9,517,095B2 and U.S. Pat. No. 8,398,635B2 have holes for screw anchoring, but the surgeon is forced to insert the screws at a particular angle and distance considering that the surgeon needs to bend the rods to accommodate the patient anatomy. This does not result in full bone containment of the screw.

The screw can be inserted within transverse angular ranges that are associated to the imposed sagittal inclination and intraosseous depth. Further, the rod to bone distance and rod curvature needed to avoid nerve compression are also variable in relation to the inclination of the plane containing the screw heads. Therefore, the aspects of the invention described herein minimize risks to the patients through the following non-limiting advantages:

screws can be compressed against the bone
rod to bone distance and direction at which this distance is imposed are decided by the surgeon and are independent from screw length and its orientation.
the rod does not need to be cut.
since the rod is hosted in a sliding attachment, the reduction of the fracture is tutored by the sliding mechanism the rod.

Thus the steps performed in instrumenting the pelvises, in existing devices are coupled in a domino sequence while the invention described herein has been conceived so each step is independent from the previous in terms of choices.

REFERENCES CITED IN THIS EXAMPLE

Apivatthakakul, T., & Rujiwattanapong, N. (2016). "Anterior subcutaneous pelvic internal fixator (INFIX), Is it safe?" A cadaveric study. Injury, 47(10), 2077-2080. https://doi.org/10.1016/j.injury.2016.08.006

Hesse, D., Kandmir, U., Solberg, B., Stroh, A., Osgood, G., Sems, S. A., & Collinge, C. A. (2015). Femoral nerve palsy after pelvic fracture treated with INFIX: A case series. Journal of Orthopaedic Trauma. https://doi.org/10.1097/BOT.0000000000000193

Morandi, M. "Max," Daily, D., Kee, C., Barton, R. S., & Solitro, G. F. (2019). Safe Supra-Acetabular Pin Insertion in Relation to Intraosseous Depth. Journal of Orthopaedic Research, (January), jor.24323.https://doi.org/10.1002/jor.24323

Example 3

Variability in Rod to Bone Distance Needed in Pelvic Subcutaneous Internal Fixation to Avoid Nerve Compression: A Tridimensional Population-Based Study
Introduction Pelvic internal fixation, has become a method for treatment of unstable pelvic ring injuries. Although successful, one complication is femoral nerve palsy from compression of the connecting rod. In light of this complication, the study described herein can evaluate sagittal inclinations of the rod and the feasibility of using a rod with a constant curvature.

Without wishing to be bound by theory, there is a connection between the sagittal inclination of the rod and the rod to bone distance, as well as single rod can be contoured with a constant curvature to be used in patients.
Methods:

Three dimensional models of pelvis CTs from a single level 1 trauma center were created and imported into a program where software superimposed a pre-contoured rod in the sagittal planes upon the pelvic slices. The sagittal inclination was deemed acceptable is no interference occurred between the area of compression risk and the rod. For each pelvis and considered sagittal rod inclination, the rod radius of curvature (ROC), minimal rod to bone distance (RTB) and transverse inclinations ($\varphi_L$ and $\varphi_R$) were measured at which the pedicle screws should be inserted to follow the direction of the smallest RTB.
Non-limiting, Exemplary Results:

The sagittal inclinations feasible for subjects herein were between about 15° to about 30°. In this sagittal range, the average RTB varied in values ranging from 4.0±0.9 mm to 25.4±11.4 mm (p<0.01). Only 46% of subjects allowed a rod with constant curvature.
Discussion and Conclusion:

Our study found that a rod to bone distance of 15 mm was not safe for every model. As well, many subject models did not allow placement of pre-contoured rod. Patient specific templating of pelvic subcutaneous internal fixation can be needed to limit complications.

Pelvic ring fractures account for 1.5% of adult fractures and 2-5% of fractures that require inpatient admission which can be from high energy trauma or standing height falls in osteoporotic patients.[1] The pelvic subcutaneous internal fixation (PSIF) is one potential treatment option for displaced pelvic ring injuries.[2-4] It avoids complications of pelvic external fixation including pin site infections and osteomyelitis, which can be as high as 50%.[5,6] Other advantages of this technique include increased stiffness and sacroiliac (SI) joint compression.[3,7-9] It can also be beneficial in the fixation of combined pelvic ring and acetabular fractures. [3,10]

Figure 13:
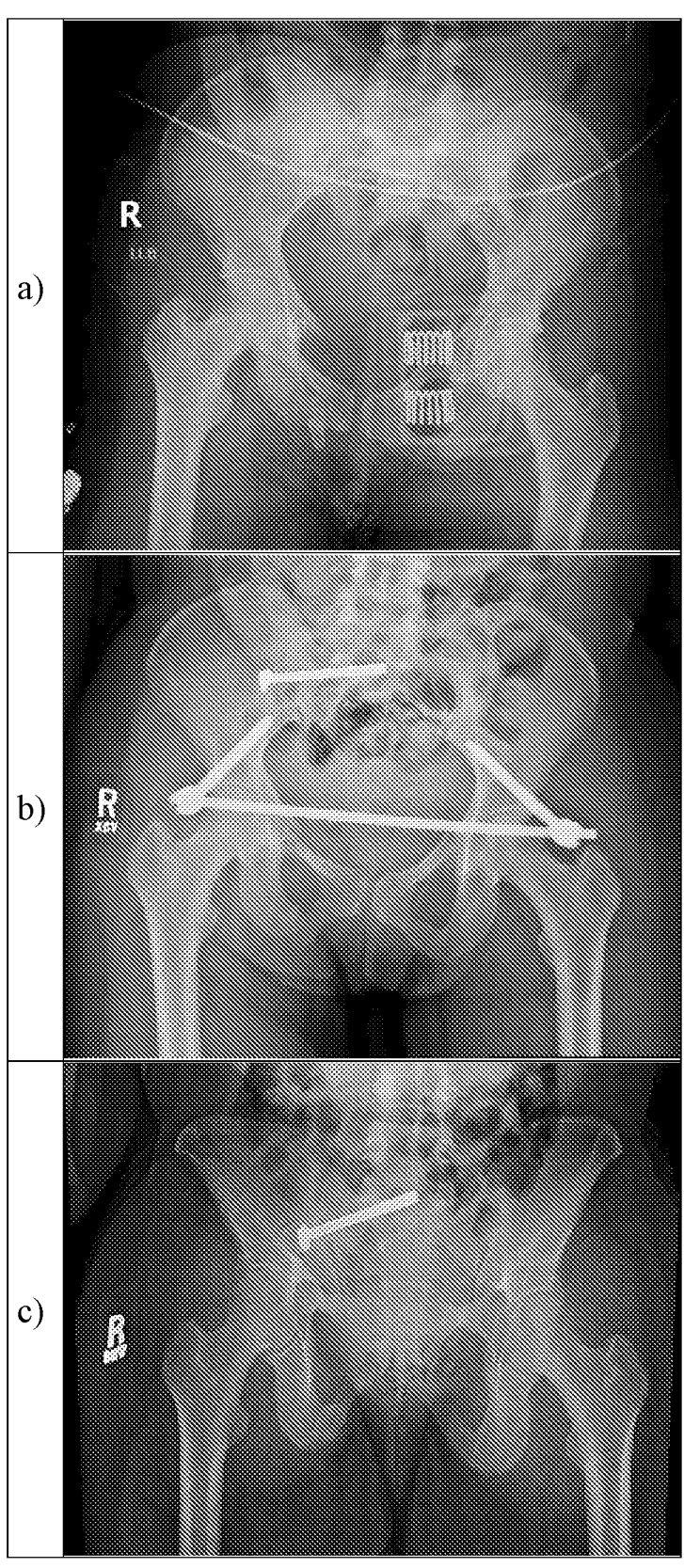
FIG. 13 is an example of a lateral compression pelvic fracture (a), stabilized (b) with pelvic subcutaneous internal fixation (PSIF), and resultant healing following removal of the construct (c).

Known complications of PSIF comprise heterotopic ossification, lateral femoral cutaneous nerve palsy, and femoral nerve and artery impingement. Heterotopic ossification associated with PSIF is can be asymptomatic, but occurs at rates of 25-30%.[11] Lateral femoral cutaneous nerve (LFCN) palsy has been documented with an incidence of 48.3% [5] and can occur at the time of rod insertion, during retraction, or from persistent tension from anteriorly placed pedicle screws and connecting bars. The original description of this technique indicates placement of the pedicle screw head 15-50 mm above the bone surface, at the level of the sartorius fascia (FIG. 13). This fascia is variable due to patient size and anatomic variability.[13] However, femoral nerve palsies and femoral artery impingement have also been reported, despite these recommended rod to bone distances.[14] Scherer et al. found that a rod to bone distance of 20-25 mm resulted in lower complication rates. They also evaluated rod to symphysis distance and found that a distance of less than 40 mm had significantly less LFCN complications, while a distance greater than 40 mm had lower rates of early implant and hardware removal.

While femoral nerve palsy is rare while using PSIF, it is a morbid complication. Despite early implant removal, femoral nerve dysfunction can persist causing quadriceps weakness and a resultant limp.[14] The femoral nerve is sensitive to compression and injury at the site of PSIF's subcutaneous rod position due to the vascular watershed. [16] In reference to rod placement, the original technique describes matching the rod with the contour of the anterior abdomen, with orientation of the rod to lie in the bikini line. Here, the anatomy is can be consistent.[17] Little attention has been paid to rod curvature with respect to complications of PSIF and there are no reportable cases found in the literature. Therefore, the study herein focuses on the rod contouring in an attempt to shed light on the morbid nature and unresolved etiology of iatrogenic femoral nerve palsy following PSIF.

Without wishing to be bound by theory, there is a connection between the sagittal inclination of the rod and the rod to bone distance, as well as a simplified approach in which the rod can be contoured with a constant curvature that is feasible for patients. Herein, we identified the influence of the conferred rod sagittal inclination on the rod to bone distance, and validated the percentage of patients that are suitable for PSIF instrumentation with a rod contoured in a constant curvature.

Materials and Methods

Patients

The study was conducted from data available at a single Level 1 trauma center. Following Institutional Reviewer Board approval, CT scans of patients in age ranging from 18 to 70 years old were chosen for the study. Pelvises with retained hardware from previous surgeries, acetabular column or ilium fractures, and scans with a slice thickness greater than 1.5 mm were excluded.

Methods

The CT data was segmented in InVesalius[18] and refined in Autodesk Meshmixer (AutoDesk Inc., San Rafael, CA)

following a published protocol.[19] The reconstructed pelvises were then analyzed in Rhinoceros 3D (Robert McNeal, Seattle, WA) using a custom-built script algorithm that standardized, among subjects, the rod contouring.

For each hemipelvis, a triangle ($\tau$) containing the femoral nerve was created to identify the body region in which compression is unwanted. This triangle was created by connecting three pelvic landmarks (FIG. 13). The first landmark (A) is the crease between the psoas major and iliacus muscles. It is known that the femoral nerve lies in this crease at the floor of the iliopsoas groove. As the femoral nerve never crosses anterior to the inguinal ligament, the second landmark (B) is chosen as the anterior superior iliac spine to designate the superior attachment of the inguinal ligament. The third landmark (C) is the inferior attachment of the inguinal ligament at the anterolateral corner of the pubic tubercle.

Figure 14:
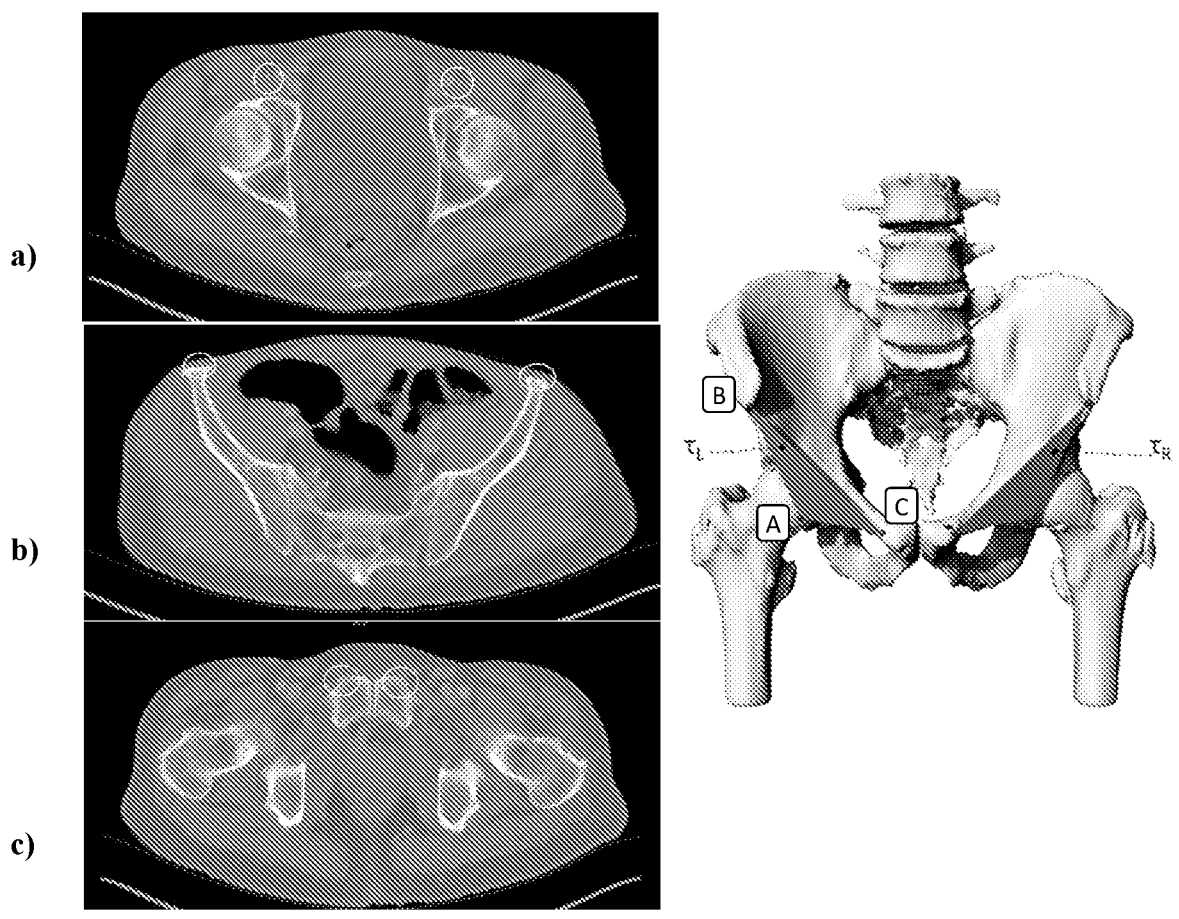
FIG. 14 provides a representation of the three landmarks used for the identification of the "safe triangle" and their respective view in the Axial CT slices: (A) is the crease between the psoas major and iliacus muscles; (B) is the anterior superior iliac spine to designate the superior attachment of the inguinal ligament; (C) is the inferior attachment of the inguinal ligament at the anterolateral corner of the pubic tubercle.

The scripted algorithm created transverse planes ($\pi_i$) at sagittal inclinations ranging from 0 to 45° in 5° intervals (FIG. 14, panel a). Rod contouring was performed for each obtained transverse plane (FIG. 14, panel b) through the intersections of the plane with the Pelvis (P), abdominal wall ($\delta$) and with the triangular region ($\tau$) (FIG. 14, panel c). For each side, circular safe regions ($C_R$ and $C_L$) centered around the arteries ($\beta_R$ and $\beta_L$) were drawn with radius equal to the distance from the centroid of the artery to the most anterior point of the triangular region. The rod (R) was then contoured as the arc tangent to the two safe regions ($C_R$ and $C_L$ and passed through the most anterior point of the abdominal wall intersection curve ($\Gamma_A$) (FIG. 14, panel c).

Methods of Assessment

In order to identify the influence of the conferred rod sagittal inclination on the rod to bone distance, we measured the rod radius of curvature (ROC) and minimal rod to bone distance (RTB) for each pelvis and for each considered sagittal rod inclination. Transverse inclinations ($\varphi_L$ and $\varphi_R$) were measured at which the pedicle screws should be inserted to follow the direction of the smallest RTB.

The percentage of patients suitable for PSIF instrumentation performed with constant curvature was evaluated through the number of subjects in which there was no interference between the pelvic bone and the contoured rod. Subjects were further classified through the measured pelvis width to abdominal wall elevation Ratio (PW-AWE Ratio) to provide guidance to the surgeons. The latter was defined as ratio between the length of the line drawn from the two iliac spines and the distance from this line and the most anterior aspect of the abdominal wall ($\delta$).

Statistical Analysis

RTB variability among subjects was evaluated with one-way analysis of variance (ANOVA). T-test with paired two samples of means were performed between consecutive sagittal inclinations, to identify the sagittal angle at which changes in RTB and rod radius curvature were observed. Both analyses were performed in Microsoft Excel (Microsoft Corporation, Redmond, WA) with a level of significance set to 0.05.

Results

Rod to Bone (RTB) Distance

Figure 15:
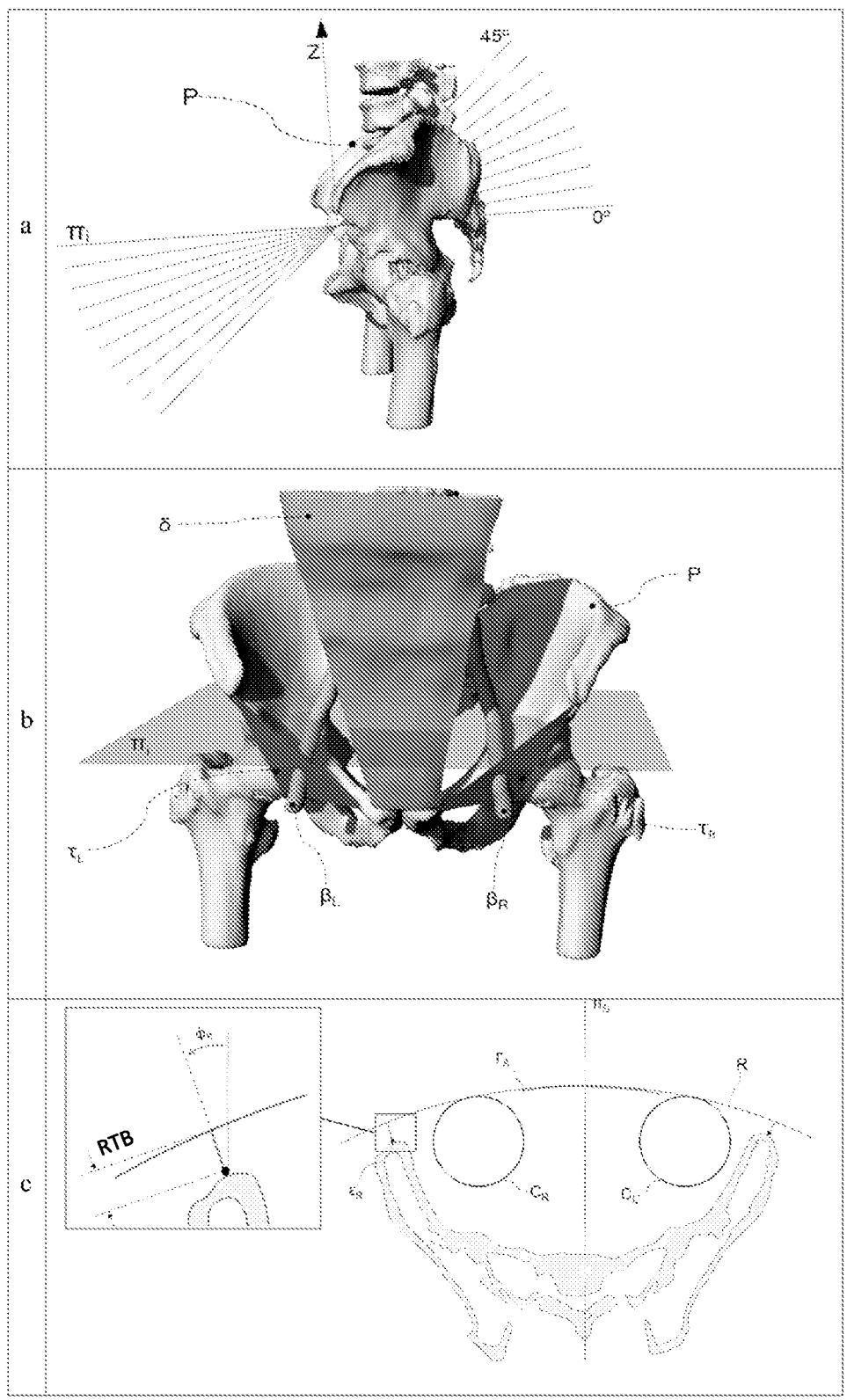
FIG. 15 provides a non-limiting illustration of the templating method used in its 3 steps of execution: (a) sectioning of the reconstructed pelvis (P) is performed through the transverse planes ($\pi$i); (b) the intersections ($\Gamma$A) of the abdominal wall ($\delta$) is identified in each of the transverse planes ($\pi$i); (c) the point of intersections ($\beta$R and $\beta$L) of the femoral arteries with the transverse planes are used as center for the circles (CR and CL) used as safe regions; In each plane, the rod R is created as the arc tangent to the two circles (CR and CL) and passing through the intersection of the abdominal wall ($\Gamma$A). For each side and each plane, the minimal rod to bone distance (dR) is evaluated as the minimal distance between the drawn arc and the bone and measured at the angle $\varphi$.

A total of 39 pelvises were analyzed and the RTB calculated for the left hemipelvis were not different from the values found for the right hemipelvis (p>0.239). The only sagittal inclinations feasible for the subjects were included between 15° to 30° (FIG. 15, panel a). In this sagittal range, the average RTB varied from subject to subject in values ranging from 4.0±0.9 mm to 25.4±11.4 mm (p<0.01). Among the subjects, the maximum recorded RTB was of 47.1 mm at 10° of sagittal inclination. The average RTB for each considered inclination decreased from 24.9±13.9 mm at 0° of sagittal inclination to a minimum value of 9.5±14.7 mm at 35° (p<0.01). Such decrease was represented by a linear relationship between sagittal inclination and RTB ($R^2$=0.345). The transition from the 35° to 40° resulted in a non-significant RTB difference (p=0.717), but the latter was feasible for 67% of the subjects (FIG. 15, panel b).

The average screw transverse inclination corresponding to the RTB distance ($\varphi$) increased from 24.7±14.5° to a peak of 43.4±9.1° respectively, for sagittal inclinations of 0° and 35° (see FIG. 3c). Each 5° increment in sagittal angle resulted in a significant variation of the screw transverse inclination (p<0.01) with exemption of insertion at 40° and 45° sagittal angles that required transverse angles of 43.1±9.1° and 42.1±9.8°, respectively (p=0.152).

Subjects Suitable for PSIF in Constant Rod Curvature

Of the considered subjects, only 46% were suitable for a rod with constant curvature. A threshold value of 4.3 for the pelvis width to abdominal wall elevation ratio (PW-AWE Ratio) was found to adequately separate the subjects that were non-suitable for a constant rod curvature with the exemption of two subjects. Both of these subjects were found to have the vasculature bundle far posterior to the entry points.

Figure 16:
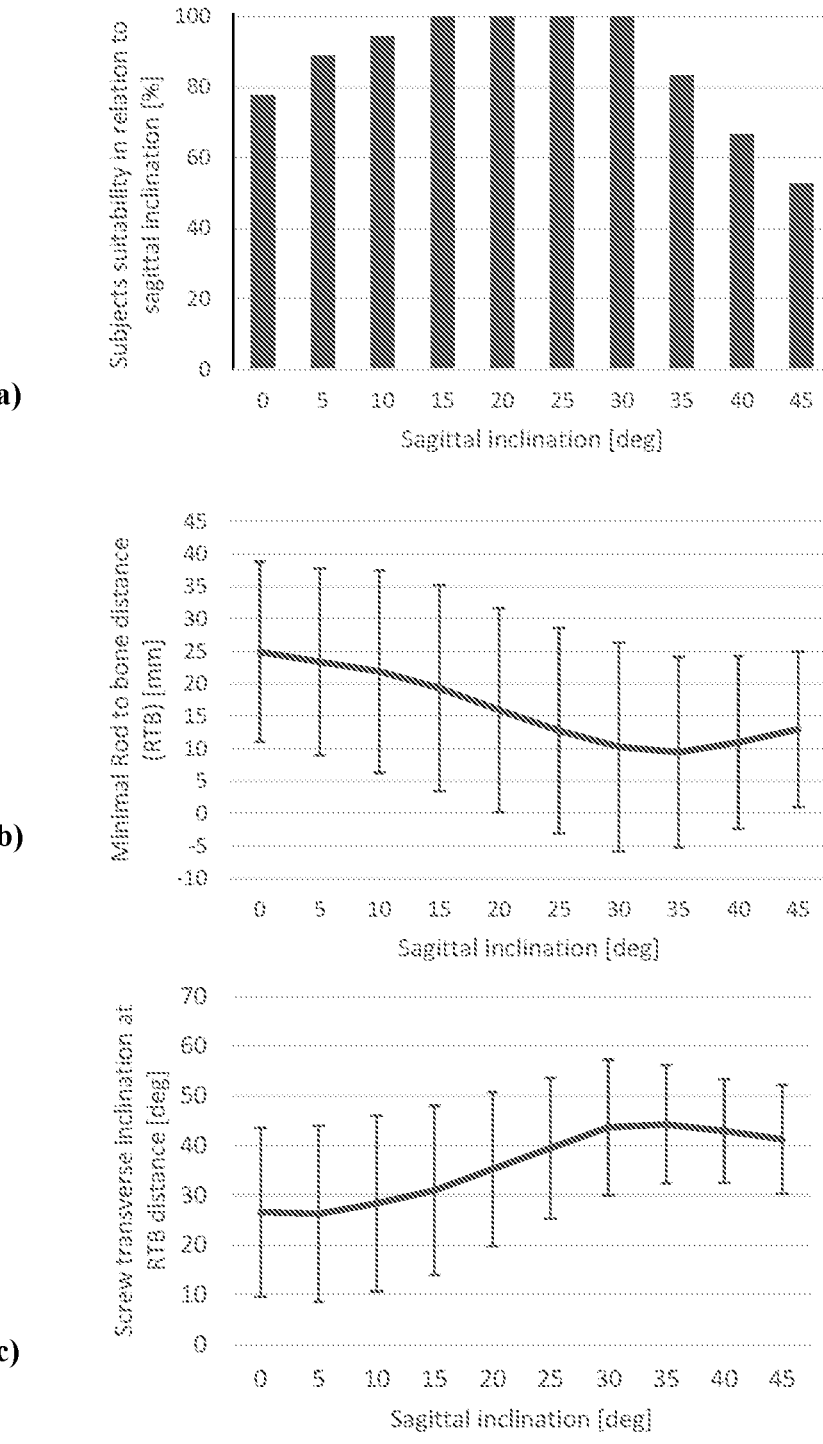
FIG. 16 shows subcutaneous internal fixation with rod of single curvature detailed in: (a) percentage of suitable subjects; (b) rod to bone (RTB) distance; and (c) transverse inclination corresponding to the measured RTB.
Figure 17:
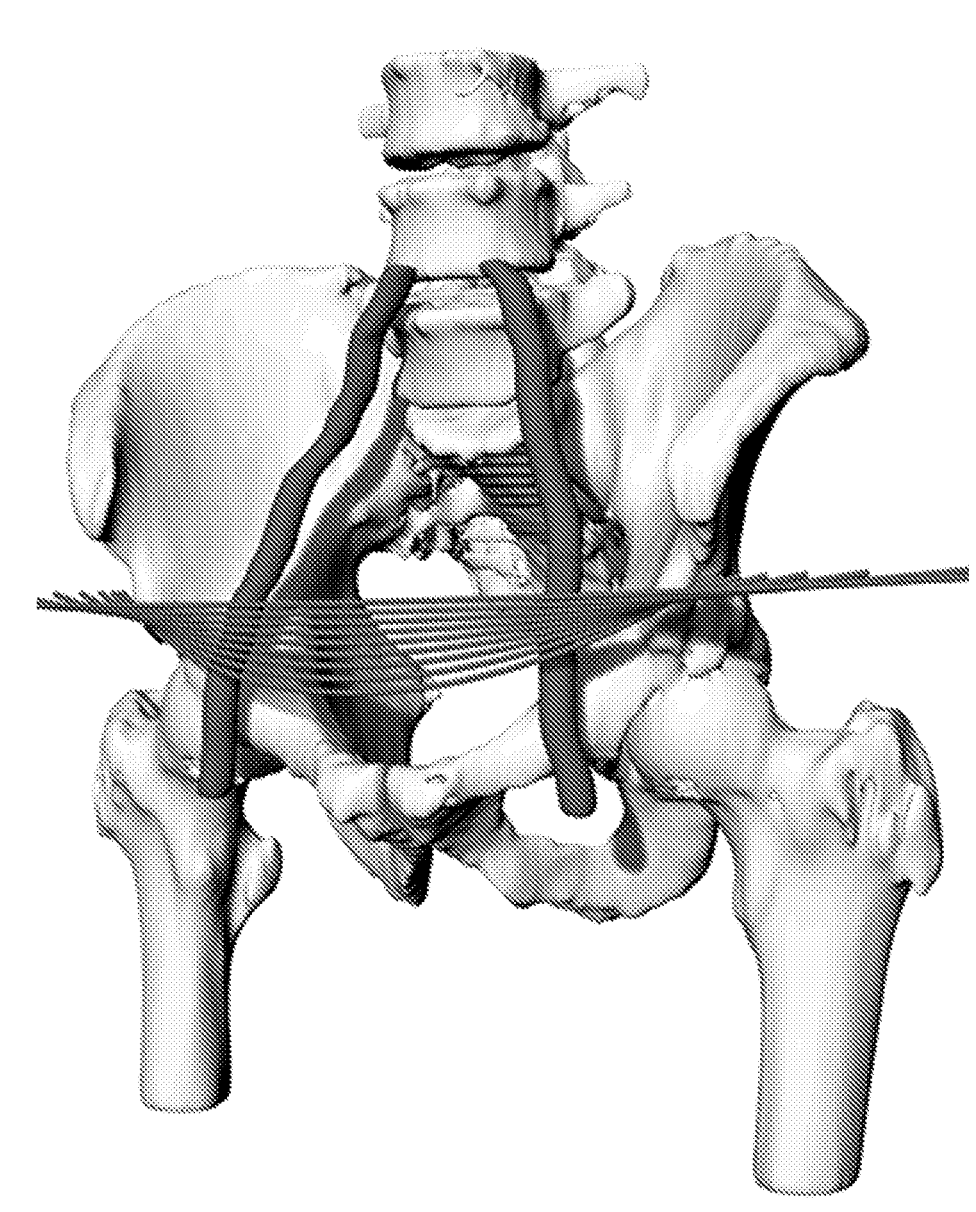
FIG. 17 shows rod contouring in relation to sagittal inclination here shown for one of the subjects (a) and average values of the rod radius of curvature found for a group of subjects (b).

Considering the sagittal inclinations between 15° and 30°, the average rod curvature showed strong variability among subjects (p<0.001) ranging from a minimal value of 140.5±13.1 mm to a maximal of 359.4±218.4. For planes containing the rods at sagittal angles from 0° to 15°, the radius of curvature was found to be 426.9±351.0 mm and 282.8±141.5 mm (p>0.072, FIG. 16, panel a). While we did not find a linear relationship between the sagittal inclination and rod curvature ($R^2$=0.186), for increased sagittal inclinations, the curvature decreased to a minimum of 164.5±41.0 mm at 35° (p<0.005). From the latter, increased sagittal inclinations did not result in significant changes of curvature (p>0.137, FIG. 16, panel b).

Discussion

Anterior subcutaneous internal fixation is a technique that is utilized for the stabilization of pelvic ring disruptions.[12, 13,19,20] On one hand, this technique offers advantages over external fixation in terms of reduced infection rates, superior stiffness, and shorter operating times. [9,21] While on the other, this technique can result in LFCN nerve irritation and heterotopic ossification. [7] The study described herein can identify proper rod contouring and was developed to rationalize the instrumentation process and systematically evaluate the relationship between rod sagittal inclination and minimal rod to bone distance (RTB). We found that rod curvature varies with sagittal inclinations. As rods were templated at more inferior inclinations, they required a smaller radius of curvature to maintain safe passage. We also found that while a linear relationship cannot be drawn between sagittal inclinations and RTB ($R^2$=0.345), a variation in sagittal inclination results in significant variations of the RTB and screw directions (p<0.01) for some of the considered angles. We found that there is variability among subjects (p<0.01).

The peak value we have found of 47.1 mm in one of the subjects was close to the maximal distance of 50 mm indicated by Vaidya [13]. The suggested rod to bone distance of 15 mm which was suggested for rods disposed along the bikini line is greater than the average values we have found for sagittal inclinations equal or greater than 25°. In a study, it was found that less complications have been associated with a distance of 20 to 25 mm while damages to the LFCN are associated with RTB distances above 40 mm. On average, for sagittal inclinations from 0° to 15°, we found values within this same range. While the average values found in this study are in alignment with values reported in existing literature, there is not a RTB distance that accommodates every subject. In addition to the previous consideration that RTB distance is associated with the habitus of the patient, [13] we have found that within a particular subject, RTB is influenced by sagittal inclination. Herein, we create a standardized approach to PSIF safe dimensioning and placement using CT data. Our initial algorithm defined the anterior aspect of the abdomen as a restriction point for defining rod curvature. Our three defining points for our rod were tangent to both neurovascular safe zones and the intersection of the anterior restriction point at the subcutaneous abdomen, as observed on CT data. Therefore, our model, at present, cannot show changes in anatomy between supine and sitting positions. We will include a two position or dynamic model in which anatomy can be modeled or better predicted in the sitting position. As the femur moves into flexion, soft tissue impingement can occur at the PSIF hardware sites and can contribute to LFCN and femoral nerve palsies. Utilizing unstable pelvises with static images cannot allow to evaluate the use of a rod with constant curvature. The indication for PSIF relates to pelvic ring and acetabular fractures which will distort normal anatomy. In particular, a large pelvic hematoma can significantly distort the location of normal anatomic structures, which can limit the applicability of the presented templating technique.

Non-Limiting Conclusions

Without being bound by theory, a minimum rod to bone distance of 15 mm can provide adequate space for avoiding impingement of the femoral artery and nerve. Our model shows that safe rod to bone distance in PSIF varies in relation to the conferred sagittal inclination of the rod and also varies among subjects. A rod to bone distance of 15 mm was not safe in every considered models. There was also a subset of models which cannot achieve safe PSIF placement with a rod of single curvature. Patient specific templating of PSIF can be needed to limit complications. The technique described herein creates a CT based technique.

REFERENCES CITED IN THIS EXAMPLE

[1] Melhem E, Riouallon G, Habboubi K, Gabbas M, Jouffroy P. Epidemiology of pelvic and acetabular fractures in France. Rev Chir Orthop Traumatol 2020; 106: 488-96. https://doi.org/10.1016/j.rcot.2020.01.004.

[2] Vaidya R. Method for minimally invasive treatment of unstable pelvic ring injuries with an internal anterior fixation and posterior iliosacral screws.pdf 2012; 2:1-8.

[3] Vigdorchik J M, Esquivel A O, Jin X, Yang K H, Vaidya R. Anterior internal fixator versus a femoral distractor and external fixation for sacroiliac joint compression and single stance gait testing: A mechanical study in synthetic bone. Int Orthop 2013. https://doi.org/10.1007/s00264-013-1890-9.

[4] Cavalcanti Kußmaul A, Greiner A, Kammerlander C, Zeckey C, Woiczinski M, Thorwächter C, et al. Biomechanical comparison of minimally invasive treatment options for Type C unstable fractures of the pelvic ring. Rev Chir Orthop Traumatol 2020; 106:43-4. https://doi.org/10.1016/j.rcot.2019.11.024.

[5] Fang C, Alabdulrahman H, Pape H C. Complications after percutaneous internal fixator for anterior pelvic ring injuries. Int Orthop 2017; 41:1785-90. https://doi.org/10.1007/s00264-017-3415-4.

[6] Vaidya R, Kubiak E N, Bergin P F, Dombroski D G, Critchlow R J, Sethi A, et al. Complications of anterior subcutaneous internal fixation for unstable pelvis fractures: A multicenter study trauma. Clin Orthop Relat Res 2012; 470:2124-31. https://doi.org/10.1007/s11999-011-2233-z.

[7] Vaidya R, Woodbury D, Nasr K. Anterior Subcutaneous Internal Pelvic Fixation/INFIX: A Systemic Review 2018; 32:24-30. https://doi.org/10.1097/BOT.0000000000001248.

[8] Yin Y, Zhang R, Li S, Su K, Hou Z, Zhang Y. Complications following internal fixator in the treatment of pelvic fracture. Orthopedics 2019. https://doi.org/10.3928/01477447-20181102-06.

[9] Vigdorchik J M, Esquivel A O, Jin X, Yang K H, Onwudiwe N A, Vaidya R. Biomechanical stability of a supra-acetabular pedicle screw Internal Fixation device (INFIX) vs External Fixation and plates for vertically unstable pelvic fractures. J Orthop Surg Res 2012; 7:1. https://doi.org/10.1186/1749-799X-7-31.

[10] Vaidya R, Blue K, Oliphant B, Tonnos F. Combined Pelvic Ring Disruption and Acetabular Fracture: Outcomes Using a Sequential Reduction Protocol and an Anterior Subcutaneous Pelvic Fixator (INFIX). J Orthop Trauma 2019. https://doi.org/10.1097/BOT.0000000000001416.

[11] Cole P A, Dyskin E A, Gilbertson J A. Minimally-invasive fixation for anterior pelvic ring disruptions. Injury 2015. https://doi.org/10.1016/50020-1383(15)30008-5.

[12] Osterhoff G, Aichner E V., Scherer J, Simmen H P, Werner C M L, Feigl G C. Anterior subcutaneous internal fixation of the pelvis—what rod-to-bone distance is anatomically optimal? Injury 2017; 48:2162-8. https://doi.org/10.1016/j.injury.2017.08.047.

[13] Vaidya R, Colen R, Vigdorchik J, Tonnos F, Sethi A. Treatment of unstable pelvic ring injuries with an internal anterior fixator and posterior fixation: Initial clinical series. J Orthop Trauma 2012. https://doi.org/10.1097/BOT.0b013e318233b8a7.

[14] Hesse D, Kandmir U, Solberg B, Stroh A, Osgood G, Sems S A, et al. Femoral nerve palsy after pelvic fracture treated with INFIX: A case series. J Orthop Trauma 2015. https://doi.org/10.1097/BOT 0.0000000000000193.

[15] Scherer J, Tiziani S, Sprengel K, Pape H C, Osterhoff G. Subcutaneous internal anterior fixation of pelvis fractures—which configuration of the InFix is clinically optimal?—a retrospective study. Int Orthop 2019; 43:2161-6. https://doi.org/10.1007/s00264-018-4110-9.

[16] Al-Ajmi A, Rousseff R T, Khuraibet A J. Iatrogenic femoral neuropathy: Two cases and literature update. J Clin Neuromuscul Dis 2010. https://doi.org/10.1097/CND.0b013e3181f3dbe7.

[17] Vaidya R, Oliphant B, Jain R, Nasr K, Siwiec R, Onwudiwe N, et al. The bikini area and bikini line as a location for anterior subcutaneous pelvic fixation: An anatomic and clinical investigation. Clin Anat 2013; 26:392-9. https://doi.org/10.1002/ca.22149.

[18] Okuyama K, Abe E, Suzuki T, Tamura Y, Chiba M, Sato K. Influence of bone mineral density on pedicle screw fixation: a study of pedicle screw fixation augmenting posterior lumbar interbody fusion in elderly patients. Spine J Off J North Am Spine Soc 2001; 1:402-7.

[19] Morandi M "Max," Daily D, Kee C, Barton R S, Solitro G F. Safe Supra-Acetabular Pin Insertion in Relation to Intraosseous Depth. J Orthop Res 2019; 37:1790-7. https://doi.org/10.1002/jor.24323.

[20] Hua X, Yan S G, Cui Y, Yin Z, Schreiner A J, Schmidutz F. Minimally invasive internal fixator for unstable pelvic ring injuries with a pedicle screw-rod system: a retrospective study of 23 patients after 13.5 months. Arch Orthop Trauma Surg 2019; 139:489-96. https://doi.org/10.1007/s00402-018-3094-7.

[21] Scheyerer M J, Zimmermann S M, Osterhoff G, Tiziani S, Simmen H-P, Wanner G A, et al. Anterior subcutaneous internal fixation for treatment of unstable pelvic fractures. BMC Res Notes 2014; 7:133. https://doi.org/10.1186/1756-0500-7-133.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed:

1. A surgical device, wherein the device comprises a bone screw, a bone screw head connector, and a rod, wherein a receiving end of the bone screw head connector is rotatably coupled to a screw head of the bone screw, wherein the rotatable coupling allows deflection of a longitudinal axis of the bone screw head connector from the longitudinal axis of the bone screw, wherein the bone screw head connector is threadably attached to a rod attachment end, wherein the threadable attachment allows adjustment of the rod attachment end's distance from the bone screw head connector, wherein the rod attachment end is configured for attachment to the rod.

2. The surgical device of claim 1, wherein the bone screw comprises a threaded body.

3. The surgical device of claim 2, wherein the screw head comprises a spherical head.

4. The surgical device of claim 1, wherein the bone screw head connector comprises a polyaxial bone screw head connector.

5. The surgical device of claim 1, wherein the rod attachment end comprises a polyaxial head.

6. The surgical device of claim 1, wherein the rod attachment end comprises a spherical head.

7. The surgical device of claim 1, wherein the rod comprises at least one receiving end, wherein the receiving end is configured to attach to the rod attachment end of the bone screw head connector.

8. The surgical device of claim 1, wherein the length of the rod is adjustable.

9. The surgical device of claim 1, wherein the rod comprises a telescoping rod.

10. The surgical device of claim 1, wherein the rod is curved.

11. The surgical device of claim 1, wherein the rod terminates at the bone screw head connector.

12. A method for implanting the surgical device of claim 1 into a subject, the method comprising:
inserting the bone screw into a bone of a subject,
coupling the bone screw head connector to the bone screw head,
determining the appropriate angle of the head of the bone screw head connector relative to surrounding anatomical structures and immobilizing the bone screw head connector;

coupling the rod to the bone screw head connector, determining the appropriate angle of the rod relative to abdominal organs and musculature, and immobilizing the rod, thereby implanting the surgical device into a subject.

13. The method of claim 12, wherein the bone comprises a pelvic bone.

14. The method of claim 12, wherein the bone is a fractured bone.

\* \* \* \* \*